United States Patent [19]

De Farcy

[11] Patent Number: 5,120,219

[45] Date of Patent: Jun. 9, 1992

[54] DENTAL CARE APPARATUS

[76] Inventor: Bertrand De Farcy, 32, Place Saint-Pierre, 49400 Saumur, France

[21] Appl. No.: 513,913

[22] Filed: Apr. 24, 1990

[30] Foreign Application Priority Data

Apr. 28, 1989 [FR] France .................. 89 05956

[51] Int. Cl.$^5$ ............................... A61C 3/02
[52] U.S. Cl. ..................................... 433/88
[58] Field of Search ......................... 433/88, 80

[56] References Cited

U.S. PATENT DOCUMENTS

| | | | |
|---|---|---|---|
| 2,825,135 | 3/1958 | Tilden | 433/88 |
| 3,718,973 | 3/1973 | Slater | 433/84 |
| 3,949,753 | 4/1976 | Dockhorn | 433/88 |
| 3,954,407 | 5/1976 | Andary et al. | 312/206 |
| 3,955,922 | 5/1976 | Moulthrop | 312/209 |
| 3,971,136 | 7/1976 | Madsen | 433/88 |
| 4,482,322 | 11/1984 | Hain et al. | 433/88 |
| 4,522,597 | 6/1985 | Gallant | 433/88 |
| 4,696,644 | 9/1987 | Goof | 433/88 |
| 4,906,187 | 3/1990 | Amadera | 433/80 |
| 4,941,298 | 7/1990 | Fernwood et al. | 433/88 |

FOREIGN PATENT DOCUMENTS

| | | | |
|---|---|---|---|
| D597288 | 1/1984 | European Pat. Off. | |
| 0209637 | 3/1968 | U.S.S.R. | 433/88 |

Primary Examiner—John J. Wilson
Attorney, Agent, or Firm—Ladas & Parry

[57] ABSTRACT

This apparatus is of the type comprising a hand instrument (5) adapted to perform a sandblasting operation by projecting a powder onto the teeth, combined with a rinsing operation by projecting a liquid.

According to the invention, the powder (300) is contained in a first receptacle (3) in which it is suspended in compressed air, whereas the rinsing liquid (400) is contained in a second receptacle (4), and there is provided a single compressor (1) which supplies compressed air to the two receptacles (3, 4), conduits (30, 40) transferring respectively the powder suspended in the compressed air and the liquid to the hand instrument (5), from where the two flows of treatment are projected by means of an intrabuccal cannula (51).

7 Claims, 2 Drawing Sheets

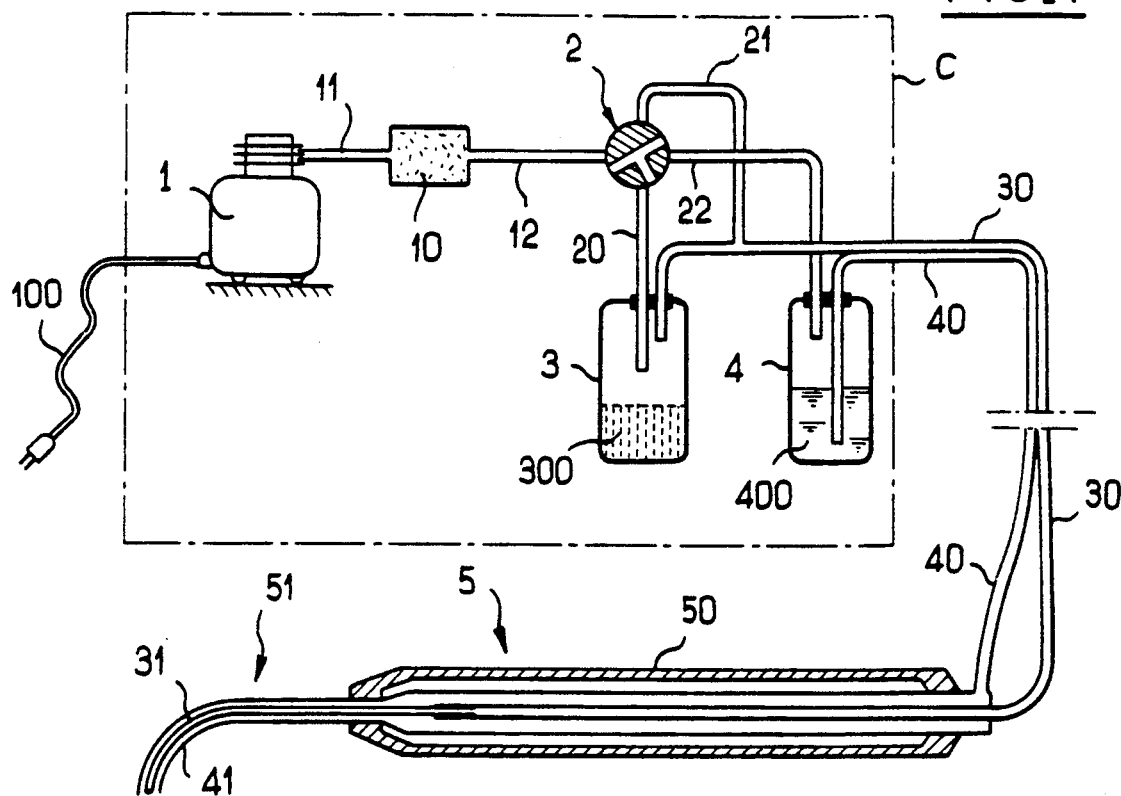
FIG_1
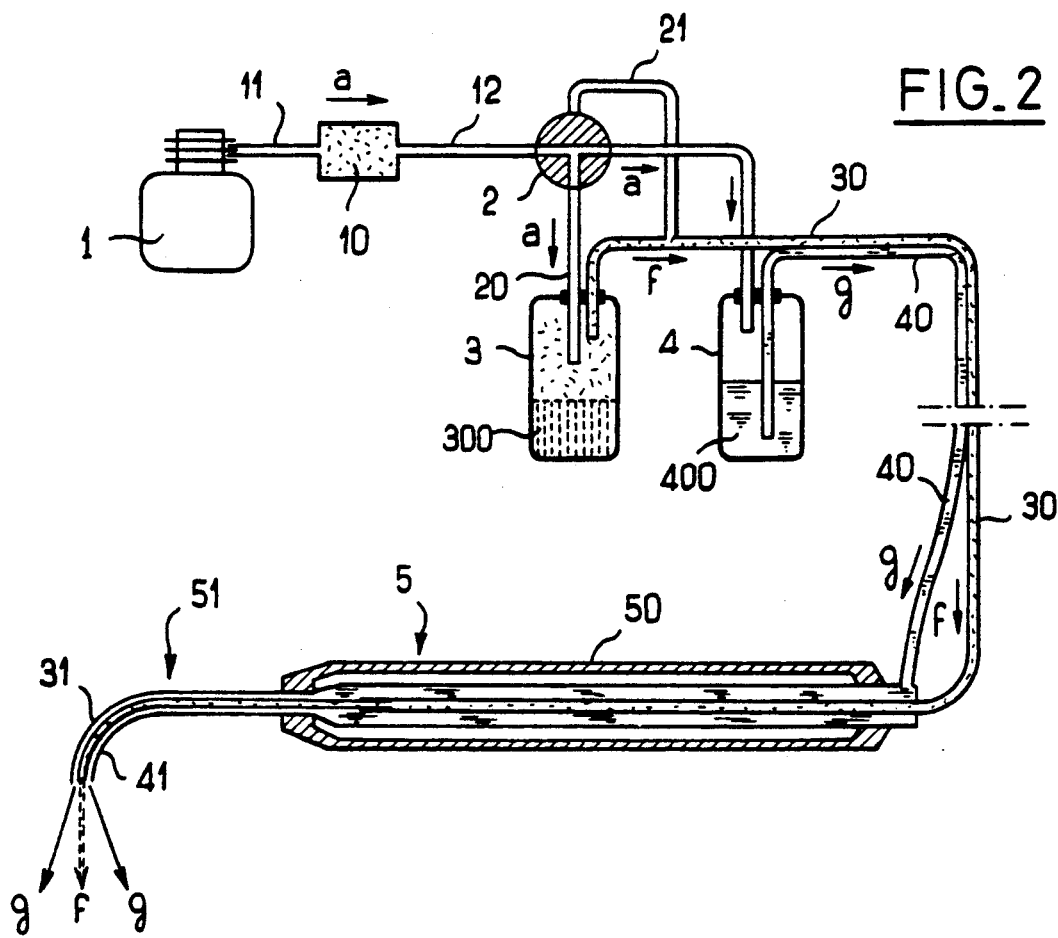
FIG_2

DENTAL CARE APPARATUS

BACKGROUND OF THE INVENTION

The present invention relates to a dental care apparatus, and more precisely to an apparatus of the type comprising a hand instrument adapted to perform a sandblasting operation by projecting a powder onto the teeth, combined with a rinsing operation by projecting a liquid.

Apparatuses of this type are already known and used in dental and stomatological offices; the hand instrument, manipulated by the practitioner, is adapted to direct onto the teeth to be treated a double flow of fluids, namely a first flow carrying particles of powder, generally of sodium bicarbonate, which are suspended in compressed air, and a second liquid flow, in this instance of pressurized water; apparatuses of this kind are described in particular in the documents FR-A-2,567,747, 2,528,693 and 2,572,925.

The hand instrument possesses an intrabuccal cannula shaped so as to project the two jets onto the patient's teeth, in particular at the base of the teeth in the region of the subgingival sulcus, in order to remove bacterial plaque, which is particularly dangerous to the periodontium. In a known embodiment, the cannula has a central conduit serving to project the bicarbonate, and an annular conduit surrounding the central conduit for projecting water (see FR-A-2,575,062).

Such an apparatus is extremely advantageous as far as hygiene is concerned owing to the fact that no part of the instrument comes into contact with the patient's teeth or mouth during treatment, thereby considerably reducing the risks of bacterial contamination; in addition, it is very efficient for the prophylaxis of infections of the periodontium, since the jet of compressed air which transports the powder particles lifts the gingival margin slightly, permitting proper and extensive sandblasting and rinsing of the bacterial plaque.

One disadvantage of this type of apparatus consists in the fact that it is necessary to have available two different external sources for supplying fluid, one of compressed air and the other of pressurized water. This constraint is unimportant when the apparatus is used in a dental or stomatological office owing to the fact that the treatment console of such an office is traditionally already equipped with these two sources of supply, as well as with the corresponding distribution pipes, which are essential to the functioning of the various instruments and tools traditionally used in dental care.

In contrast, this constraint is a very considerable disadvantage insofar as it prevents virtually all domestic use, private individuals generally not possessing a compressed air inlet conduit in their bathroom.

Another disadvantage of the known apparatuses lies in the fact that it is not possible to use any other liquid than water for rinsing, even where it would occasionally be advantageous to use liquids having an antiseptic or medicamentous action.

The object of the invention is to solve these problems by proposing, as a result of minor and inexpensive modifications, to improve the known apparatus in order to turn it into an apparatus intended for domestic use, which is easy to use and in which it is possible to employ any appropriate liquid, even of syrupy consistency, for rinsing.

SUMMARY OF THE INVENTION

To this end, the apparatus according to the invention which, like the apparatuses known hitherto, comprises a hand instrument adapted to perform a sandblasting operation by projecting a powder onto the teeth, combined with a rinsing operation by projecting a liquid, the powder being contained in a first receptacle in which it is suspended in compressed air, and means being provided for conveying the mixture of air and powder to said hand instrument, whereas other means are provided for conveying the liquid to the latter, is distinguished in that it comprises a portable compressor capable of supplying compressed air, on the one hand, to said first receptacle and, on the other hand, to a second receptacle containing the liquid, so as to pressurize this receptacle and to drive out the liquid therefrom toward the hand instrument.

Furthermore, according to a number of advantageous but non-limiting features of the invention:

the apparatus comprises a three-way valve mounted at the outlet of the compressor and capable of being brought selectively to a position in which the compressor supplies compressed air to the two receptacles at once and to a position where it supplies compressed air only to the second receptacle;

the hand instrument is provided with an intrabuccal projection cannula which is composed of two coaxial conduits, namely a central conduit for projecting the mixture of compressed air and powder and an annular conduit, surrounding said central conduit, for projecting the liquid;

the apparatus comprises a dehumidifying filter which is mounted at the outlet of the compressor;

the apparatus is equipped with a device for sterilizing a toothbrush, said device consisting of an ozone generator connected to a receptacle intended to receive the toothbrush, this generator being fed with air by said compressor;

this sterilizing device includes an ultrasound generator;

all the constituent elements of the apparatus, with the exception of the hand instrument, are accommodated in a small self-contained portable box.

Other features and advantages of the invention will emerge from the description and the accompanying drawings which present two preferred embodiments thereof.

DESCRIPTION OF THE DRAWINGS

In these drawings:

FIG. 1 is a general diagrammatic view of the first embodiment;

FIGS. 2 and 3 are similar views showing the apparatus during the sandblasting and rinsing operations respectively;

DESCRIPTION OF PREFERRED EMBODIMENTS OF THE INVENTION

Figure 3:
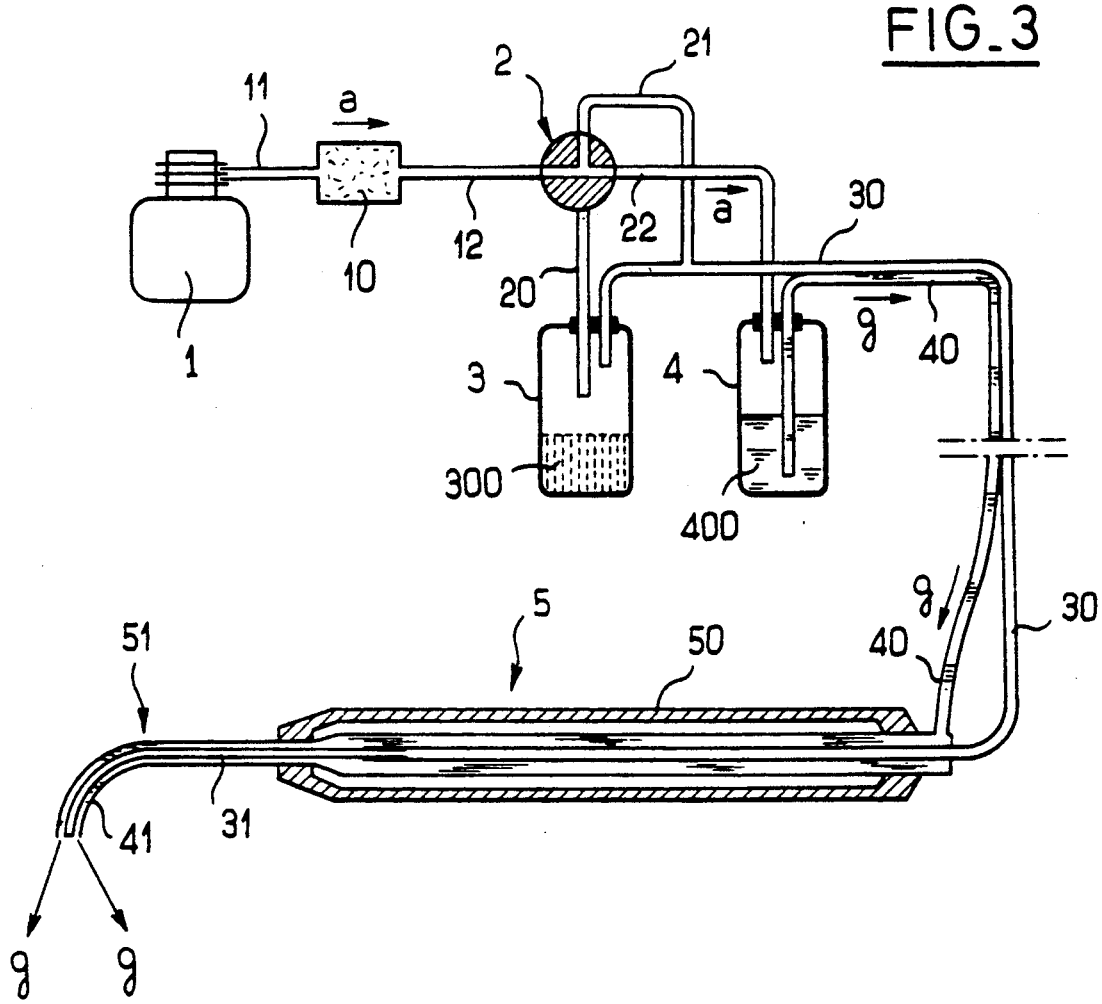

In the figures, the reference 1 designates an electric compressor, adapted to be connected to the mains (240 V a.c.) by means of a cable 100. The compressor 1 supplies compressed air at a pressure of the order of 2 bars, with a flow rate of the order of 15 to 20 liters per minute. Mounted on the outlet conduit 11 of the compressor is a dehumidifying filter 10, of known type, capable of collecting the small droplets of water which may be suspended in the air supplied by the compressor, so that the air leaving this filter 10 through a conduit 12 is absolutely dry.

Mounted on the conduit 12 is a three-way valve 2. The first outlet 20 of the valve 2 is connected, in a sealed manner, to a first receptacle 3, inside which it emerges; the receptacle 3 contains a certain quantity of powder intended for the sandblasting, such as sodium bicarbonate. It will be noted that the conduit 20 penetrates fairly deeply inside the receptacle 3. Another conduit 30, which penetrates less deeply into the receptacle, is connected, likewise in a sealed manner, to the same receptacle. This conduit feeds a hand instrument 5 which will be described hereinbelow.

The second outlet 22 of the three-way valve 2 feeds, in a similar manner to the conduit 20, a second receptacle 4 which contains a rinsing liquid 400; in the same way, an outlet conduit 40, which feeds the hand instrument 5, is connected to the receptacle 4. It will be noted, however, that the inlet conduit 22 does not penetrate very deeply into the receptacle 4 so as not to come into contact with the liquid 400; in contrast, the outlet conduit 40 is immersed in this liquid.

The third outlet conduit 21 of the valve 2 is connected to the conduit 30 at the outlet of the first receptacle 3.

All the constituents of the apparatus which has just been described are accommodated in a small box designated C and represented by a rectangle in broken lines, this small box being easily transportable and self-contained.

In the figures, the hand instrument 5 is shown to a larger scale than the constituents located in the small box C in order thereby to facilitate understanding of the drawing.

The instrument 5 comprises a handle 50 and an intra-buccal cannula 51, the shape of which makes it possible to have access to the interior of the mouth and to direct the two flows of treatment to the base of the teeth.

As is known per se, one of the constituent conduits 31 of the cannula 51 is a small central conduit, which is connected to the conduit 30 linked to the first receptacle 3; the other conduit 41 is an annular conduit, surrounding the conduit 31, to which is connected the conduit 40 linked to the second receptacle 4. The conduits 30 and 40 are, of course, flexible conduits, allowing free movement of the instrument; in contrast, the constituent conduits 31, 41 of the cannula are rigid.

An explanation will now be given of the way in which this apparatus is used, firstly to carry out a sandblasting operation and then to perform an operation for rinsing the teeth.

To switch on the apparatus, it is sufficient to electrically connect the compressor 1 to the mains supply of the user's home. The user has made sure that each of the receptacles 3 and 4 are provided with sodium bicarbonate and rinsing liquid respectively, this liquid being, for example, ordinary water, distilled water or an aqueous solution of an antiseptic or medicamentous product.

In order to perform the sandblasting, he places the three-way valve 2 in the position of FIG. 2 and switches on the compressor by means of an appropriate switch (not shown) preferably located on the handle 50. Holding the instrument 5 in one hand, he introduces the cannula into his (half-open) mouth and moves the end of this cannula close to the area to be treated, directing it toward the base of the teeth.

The compressor supplies compressed air which, after dehumidification by the filter 10, reaches the receptacle 3 where it causes the agitation and suspension of the bicarbonate particles 300 situated in the receptacle. At the same time, compressed air also reaches the receptacle 4, above the liquid 400. The arrival of the compressed air in the two receptacles 3, 4 is illustrated by the arrows a in FIG. 2. As a result of the excess pressure prevailing in the receptacles, the compressed air charged with bicarbonate powder particles leaves the receptacle 3 and is transferred through the conduit 30 to the hand instrument 5 where it penetrates into the cannula central element 31 to be projected outside the latter onto the dental area to be treated; the flow of air charged with powder particles in the apparatus is illustrated by the arrows f in FIG. 2. At the same time, the pressurizing of the receptacle 4 by the compressed air drives out the liquid contained therein, which is transferred through the conduit 40 to the hand instrument 5; in this instrument, it penetrates into the peripheral conduit 41 of the cannula and is projected onto the area to be treated in a conical jet surrounding the central jet of powder particles (arrows g).

By striking the tooth with a sandblasting action, the bicarbonate particles remove the bacterial plaque therefrom. The bicarbonate is instantaneously dissolved by the rinsing liquid, thus preventing the formation of a cloud of powder and causing the tooth to be washed and rinsed. Of course, from time to time, the user spits out the mixture consisting of the solution of the sandblasting powder in the rinsing liquid.

As already stated hereinabove, the compressed air, which serves as an agent for transporting the sandblasting powder, has the effect of lifting the gingival margin at the base of the tooth, allowing the sandblasting and rinsing products to gain proper access to the base of the tooth where the bacterial plaque most dangerous to the periodontium is generally found.

By placing the valve in the position of FIG. 3, it is possible for the user to carry out a simple rinsing of the teeth, in particular so as to get rid of the solid debris which may be located in the interdental spaces, the apparatus then functioning like a traditional waterjet apparatus but under a lower pressure which is less aggressive to the gingiva. In this case, the compressed air which reaches the receptacle 3 merely has the effect of causing an agitation of the powder particles therein, these particles not being able to escape from said receptacle (closed conduit 20). However, this compressed air drives out the particles located in the conduit 30, cleaning the latter efficiently and making it available for subsequent use. In fact, if bicarbonate particles remained in the conduits beyond the period of use of the apparatus, there would be a risk of moisture being absorbed and, owing to the formation of an amalgam, of these conduits being blocked.

The rinsing operation (arrows g) is effected in the same way as during the sandblasting-rinsing operation described with reference to FIG. 2; the cannula 51 emits a single treatment jet, in this instance a conical liquid jet.

The presence of the filter 10 in the circuit makes it possible, of course, to protect the bicarbonate 300 which, as already stated, is very sensitive to water, from moisture.

Owing to the fact that the liquid is driven out of the second receptacle 4 by compressed air (instead of being transported by a pump), it is possible to use liquids of various, more or less liquid, even viscous or syrupy, consistencies, thereby increasing the range of products which may be employed.

In a variant, the bicarbonate receptacle could consist of a removable cartridge accommodated inside the handle 50 of the hand instrument 5, and rechargeable or replaceable when empty. Such a solution, which has in particular the advantage that the bicarbonate circulates only in the intrabuccal cannula and therefore solves the problems of blocking the conduits, can be implemented in a simple manner in practice by means whose design lies within the capabilities of a person skilled in the art.

Figure 4:
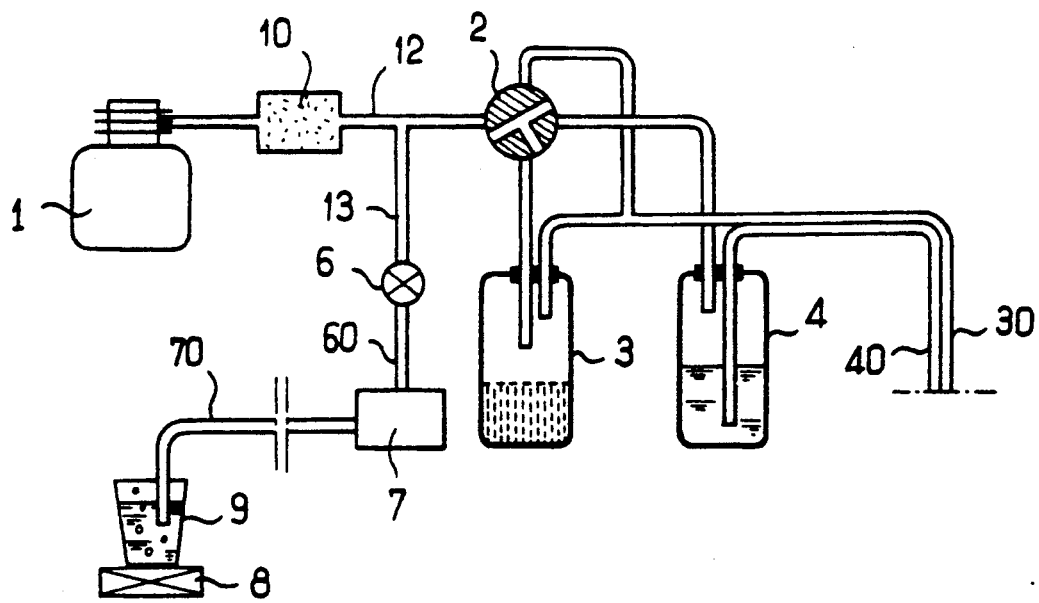
FIG. 4 is a diagrammatic view of a second embodiment of the apparatus, equipped with a sterilizing device for a toothbrush.

In the second embodiment shown in FIG. 4, all the components supplying the powder and the rinsing liquid to the hand instrument (which has not been shown again so as not to overload this figure unnecessarily) are identical to those of the first embodiment. In this variant, the outlet conduit 12 of the filter 10 has a branch 13; the latter supplies compressed air, via an ordinary valve 6 (faucet) to an electronic device 7 for manufacturing ozone from the surrounding air, of the type known per se. The device 7 supplies ozone through a conduit 70 to a receptacle 9 which is carried by a support 8 forming part of the apparatus; this support is, for example carried by the small box C. The receptacle 9 may consist simply of a sterilizing glass intended to receive the user's toothbrush. Thus, during the sandblasting and/or rinsing treatment, the compressed air supplied by the compressor 1 is sent, if the faucet 6 is open, to the device 7 which produces ozone inside the receptacle 9, thus sterilizing the toothbrush by destroying certain microbial germs which may be lodged between the bristles of this brush. In a variant, the supporting device 8 may consist of an ultrasound generator of known type, which sterilizes both the liquid contained in the receptacle 9 and the toothbrush located therein. In this embodiment, the apparatus therefore constitutes not only an apparatus for dental care by sandblasting and rinsing of the teeth, but also a unit for sterilizing the toothbrush, so that the brushing of the teeth by the user complements the treatment effectively.

In a variant, it may be advantageous to provide a functional interconnection between the valve 2 and the on-off control of the compressor, in such a way that the latter cannot be turned off until the conduit 30 has been flushed.

It may be envisaged to heat the air leaving the compressor slightly, for example by means of a heating resistor accommodated in a sleeve which would be provided on the conduit 12. This would have the effect of making the sandblasting jet more agreeable, and also of lessening the harmful effect of moisture contained in the air on the highly hydrophilic bicarbonate powder.

What is claimed is:

1. A dental care apparatus comprising a hand instrument (5) adapted to perform a sandblasting operation by projecting a powder (300) onto the teeth along with a liquid (400) for rinsing, the apparatus comprising a first receptacle (3) for receipt of a powder to be projected, a second receptacle (4) for receipt of a liquid to be projected, first and second conduit means for separately connecting said first and second receptacles, respectively, to said hand instrument, a portable air compressor (1), and means (2) for supplying compressed air from said compressor simultaneously to both said receptacles for conveying powder mixed with compressed air from said first receptacle and liquid from said second receptacle to said hand instrument for simultaneous projection therefrom.

2. The dental care apparatus as claimed in claim 1, which comprises a three-way valve (2) mounted at the outlet of the compressor (1) and capable of being brought selectively to a position in which the compressor supplies compressed air to the two receptacles (3, 4) and to a position where it supplies compressed air only to the second receptacle (4).

3. The dental care apparatus as claimed in claim 1, wherein the hand instrument (5) is provided with an intrabuccal projection cannula composed of two coaxial conduits, namely a central conduit (31) for projecting the mixture of compressed air and powder and an annular conduit (41), surrounding the central conduit (31), for projecting the liquid.

4. The dental care apparatus as claimed in claim 1, which comprises a dehumidifying filter (10) mounted at the outlet of the compressor.

5. The dental care apparatus as claimed in claim 1, which is equipped with a device for sterilizing a toothbrush, said device consisting of an ozone generator (7) connected to a receptacle (9) intended to receive the toothbrush, this generator being fed with air by said compressor (1).

6. The dental care apparatus as claimed in claim 5, wherein said sterilizing device includes an ultrasound generator (8).

7. The dental care apparatus as claimed in claim 1, wherein all of its constituent elements (1, 2, 3, 4, 6, 7), with the exception of the hand instrument, are accommodated in a small self-contained portable box (C).

* * * * *